United States Patent [19]

Schmidhammer et al.

[11] Patent Number: 5,068,475
[45] Date of Patent: Nov. 26, 1991

[54] PROCESS FOR PURIFYING UNREACTED 1,2-DICHLOROETHANE FROM A 1,2-DICHLOROETHANE PYROLYSIS PROCESS

[75] Inventors: Ludwig Schmidhammer, Haiming; Klaus Haselwarter, Emmerting; Hermann Klaus, Marktl; Klaus-Peter Mohr, Burghausen, all of Fed. Rep. of Germany

[73] Assignee: Wacker-Chemie GmbH, Munich, Fed. Rep. of Germany

[21] Appl. No.: 681,186

[22] Filed: Apr. 5, 1991

[30] Foreign Application Priority Data

Apr. 19, 1990 [DE] Fed. Rep. of Germany ....... 4012538

[51] Int. Cl.$^5$ ............................................. C07C 17/38
[52] U.S. Cl. .................................................... 570/262
[58] Field of Search ......................................... 570/262

[56] References Cited

U.S. PATENT DOCUMENTS 4,188,347  2/1980  Schmidhammer et al. ........ 570/262

Primary Examiner—Howard T. Mars
Assistant Examiner—Kimberly J. Kestler
Attorney, Agent, or Firm—Burgess, Ryan & Wayne

[57] ABSTRACT

The invention relates to a process for purifying unreacted 1,2-dichloroethane from a 1,2-dichloroethane pyrolysis process by chlorinating the benzene produced as a by-product and removing the chlorination products by distillation.

3 Claims, No Drawings

PROCESS FOR PURIFYING UNREACTED 1,2-DICHLOROETHANE FROM A 1,2-DICHLOROETHANE PYROLYSIS PROCESS

The invention relates to a process for purifying unreacted 1,2-dichloroethane from a 1,2-dichloroethane pyrolysis process by chlorinating the benzene produced as a by-product and removing the chlorination products by distillation.

In the incomplete pyrolysis of 1,2-dichloroethane to give vinyl chloride and hydrogen chloride, benzene, inter alia, is produced which, due to its boiling point, accumulates in the bottom product from the vinyl chloride column, the unreacted 1,2-dichloroethane, during the subsequent distillative work-up of this cracking gas mixture (HCl removal in the HCl column, VC and EDC removal in the downstream VC column and finally removal of low- and high-boiling impurities from the unreacted EDC in the downstream low- and high-boiling component column). Depending on the cracking conditions or work-up of the unreacted 1,2-dichloroethane to give pure 1,2-dichloroethane, which can be recycled into the pyrolysis process, more or less considerable accumulation of benzene takes place in the 1,2-dichloroethane, which extremely adversely affects the kinetics of the pyrolysis process.

It is true that the literature (Ullmann, 4th Edition, Volume 9 (1975), page 448) describes benzene as being only a weak inhibitor in the pyrolysis of 1,2-dichloroethane to give vinyl chloride and hydrogen chloride, the inhibitor effect of a substance being regarded therein, according to the definition, as being weak if concentrations of above 500 ppm must be present in the 1,2-dichloroethane so that the inhibitor effect is detectable to a significant extent.

However, if unreacted 1,2-dichloroethane is circulated after the pyrolysis and sent back to the pyrolysis after work-up, benzene concentrations of up to 5000 ppm by weight or more can occur in the 1,2-dichloroethane to be cracked, and the inhibitor effect of benzene then becomes clearly apparent. This accumulation of benzene occurs, in particular, if, after the pyrolysis according to the process of EP-A 2501 (U.S. Pat. No. 4188347), the unreacted 1,2-dichloroethane is pretreated (by-product removal by a chlorination step and a subsequent dechlorination step in the presence of hydroxyl-containing aromatic compounds) and, in accordance with EP-A 180998, worked up in an energy-saving manner by freeing only a small part stream of the pretreated unreacted 1,2-dichloroethane from low-boiling components before feeding to the pyrolysis unit, for example in accordance with DE-A 2445371 (U.S. Pat. No. 3998706).

In the pyrolysis itself, in addition, the content of benzene in the cracking gas mixture also increases with increasing conversion. An increase in the pyrolysis temperature to compensate for the inhibitor effect of the benzene necessarily results, as a consequence, in increased cracking tube wall temperatures. These in turn result in increased formation of benzene and other by-products, which can only be separated from the vinyl chloride formed with very great difficulty, but have an extremely adverse effect on the polymerization of vinyl chloride. Furthermore, the increased cracking tube wall temperatures result in increased coke formation. These increased coke depositions in the cracking tubes reduce the furnace run times and thus also the plant capacities.

In addition, the considerable thermal insulation effect of such coke deposits means that further increased cracking tube wall temperatures are necessary to compensate for the insulation effect of the coke by increasing the temperature difference between tube wall and product. Very generally, increased wall temperatures also promote high-temperature corrosion of cracking tube material by hydrogen chloride attack, which reduces the service lives of the cracking tubes (increased maintenance costs) or, in the most unfavorable cases, it is even possible for extremely dangerous operating states to occur due to tube cracks (danger to personnel, plant and environment).

The problem of benzene accumulation has recently come very much to the fore since energy-saving vinyl chloride preparation processes with the highest possible plant throughputs, such as, for example, the procedure just mentioned for the work-up of unreacted 1,2-dichloroethane, are in the meantime being pursued more and more. However, increased accumulation of benzene in 1,2-dichloroethane is an unavoidable result.

Removal of benzene from 1,2-dichloroethane by a purely distillative method is excluded from the outset for economic reasons since the very close boiling points would require considerable technical complexity and considerable energy.

It is well known from the literature that benzene can be converted into much higher boiling chlorinated aromatic compounds in the presence of catalytically active halogen-transfer agents. An example of an inexpensive halogen-transfer agent is iron(III) chloride, which is used in anhydrous, pulverulent to finely particulate form, but can also be generated in situ by reacting chlorine and metallic iron.

The latter procedure is described in German Patent 1493381 (U.S. Pat. No. 3366457). In a continuous procedure, an excess of benzene is reacted with chlorine in the presence of metallic iron to give monochlorobenzene. German Patent 558068 describes a process in which an excess of benzene is reacted with chlorine in the presence of metallic iron in the form of Raschig rings and iron wire in the vapor phase to give monochlorobenzene.

These procedures have the disadvantage that massive concentrations of iron(III) chloride of several thousand ppm, based on 1,2-dichloroethane, are necessary to chlorinate benzene at high dilutions (benzene is usually present in unreacted 1,2-dichloroethane in the concentrate range from 1000 to 8000 ppm by weight) and to achieve adequate chlorine conversions under moderate reaction conditions. However, the solubility of anhydrous $FeCl_3$ in dry 1,2-dichloroethane at a water content of less than 10 ppm by weight is only from about 350 to 600 ppm by weight, depending on the exposure time, and is thus inadequate.

DE-A 1568298 (GB-A 1184576) discloses that the solubility of $FeCl_3$ in 1,2-dichloroethane can be increased by a factor of about 10 by using iron(III) oxide in place of metallic iron and/or iron(III) chloride. The reason for this is the water which forms due to the reaction between iron(III) oxide and hydrogen chloride and obviously functions as a strong solubilizer. NL-A 7215333 teaches to employ benzene containing 200 ppm of water for the chlorination of benzene using metallic iron. However, these procedures have the disadvantage that the presence of water makes the reaction medium highly corrosive, which necessitates an expensive corrosion-resistant design of the apparatuses used.

The object of the invention was to develop a process for purifying unreacted 1,2-dichloroethane from a 1,2-dichloroethane pyrolysis process which results in the removal of benzene from 1,2-dichloroethane by the simplest possible means and the prevention of accumulation of benzene in 1,2-dichloroethane to concentrations greater than 500 ppm by weight.

Surprisingly, chlorination under moderate reaction conditions and using minimal excesses of chlorine, based on the benzene content in the unreacted 1,2-dichloroethane, in the presence of finely divided iron catalyst filling the entire reaction space results in virtually complete conversion of benzene into the corresponding chlorination products, which can then easily be removed by distillation. This is all the more surprising since the concentration of catalytically active iron-(III) chloride, which dissolves in the 1,2-dichloroethane during the process, is also only from 350 to 600 ppm by weight in this procedure.

The invention relates to a process for purifying unreacted 1,2-dichloroethane produced at the bottom of the vinyl chloride column in the preparation of vinyl chloride due to incomplete pyrolysis of 1,2-dichloroethane, which comprises a) bringing unreacted 1,2-dichloroethane recovered from the pyrolysis of 1,2-dichloroethane into contact with liquid and/or gaseous chlorine in a chlorination reactor in the liquid phase at a residence time of 20 to 150 minutes, at temperatures of from 20 to 80° C., in the presence of an iron catalyst having a bulk density of from 0.1 to 0.5 g/cm$^3$ and filling the entire reaction space, in such amounts that the unreacted 1,2-dichloroethane leaving the reactor contains excess, free chlorine in dissolved form in concentrations of from 20 to 200 ppm by weight, based on unreacted 1,2-dichloroethane, and b) purifying the 1,2-dichloroethane treated with chlorine in accordance with a) by acid and alkali washing and by distillative removal of the low- and high-boiling components.

The process according to the invention for purifying unreacted 1,2-dichloroethane from pyrolysis is carried out using the product from the bottom of the vinyl chloride column after removal of hydrogen chloride and vinyl chloride from the cracking gas mixture of the pyrolysis of 1,2-dichloroethane. The bottom product is transferred into a reactor, the flow rate in the reactor being from 0.01 to 0.1 cm/s, preferably from 0.03 to 0.06 cm/s, in each case based on the free reactor crosssection. The residence time in the reactor is from 20 to 150 minutes, preferably from 40 to 80 minutes, in each case based on the empty reactor space.

Before entering the reactor or alternatively only after entering the reactor, preferably before entering the reactor, the 1,2-dichloroethane stream is admixed with liquid and/or gaseous chlorine. In each case, the 1,2-dichloroethane stream should be brought into contact with chlorine in such amounts that the 1,2-dichloroethane stream leaving the reactor contains excess free chlorine, in dissolved form, in concentrations of from 20 to 200 ppm by weight, preferably from 50 to 100 ppm by weight based on 1,2-dichloroethane.

The chlorination reaction takes place in the reactor in the liquid phase, at temperatures of from 20 to 80° C., preferably from 30 to 50° C. The entire reaction space is filled with a finely divided iron catalyst having a bulk density of from 0.1 to 0.5 g/cm$^3$, preferably from 0.2 to 0.3 g/cm$^3$. Particularly suitable catalysts are finely divided iron turnings, iron baskets and/or steel wool. In principle, it is also possible to use iron baskets or steel wool in very finely divided form, i.e. having bulk densities of less than 0.1 g/cm$^3$. However, the danger of reactor blockage cannot be excluded in continuous flow processes.

The process according to the invention is preferably carried out fully continuously, but can also be carried out semicontinuously if, for example, the accumulation of benzene is only relatively low due to particular boundary conditions.

After treatment with chlorine, the 1,2-dichloroethane phase is freed from the iron chloride and hydrogen chloride formed by acid and alkaline washing. The acid washing can be carried in a conventional manner by means of dilute hydrochloric acid; the alkaline washing can be carried out using aqueous ammonia or dilute sodium hydroxide solution. After removal of water and low-boiling impurities by distillation, the 1,2-dichloroethane phase is fed to a high-boiling component column, in which the high-boiling impurities, including the chlorinated aromatic compounds produced during the benzene chlorination, are removed. The 1,2-dichloroethane prepared in this way can then be fed back to the pyrolysis process.

In a particularly preferred embodiment of the process according to the invention, the cracking product mixture from the cracking of 1,2-dichloroethane is first, after the removal of hydrogen chloride and vinyl chloride, treated, analogously to the procedure in the EP-A 2501, with from 0.0001 to 0.01% by weight, based on unreacted 1,2-dichloroethane, of hydroxyl-containing aromatic compounds, and subjected to a chlorination step and subsequent dechlorination step at temperatures between 0 and 80° C. and pressures of from 0.5 to 6 bar. Only a small part stream of, preferably, up to 20% by weight of the 1,2-dichloroethane phase treated in this way is then treated with chlorine in accordance with the process according to the invention and then purified by acid and alkaline washing. This part stream is then, together with crude 1,2-dichloroethane from the direct chlorination and/or oxychlorination of ethylene, preferably analogously to the procedure of DE-A 2445371, freed from low-boiling components and passed to the high-boiling component column. The main stream of the 1,2-dichloroethane phase pretreated in accordance with EP-A 2501, preferably at least 80% by weight, is passed directly to the high-boiling component column, avoiding the chlorination step, the washer and the low-boiling component separation step.

The procedure according to the invention makes it possible to keep the benzene content in pure 1,2-dichloroethane removed from the head of the high-boiling component column, and passed to the pyrolysis of 1,2-dichloroethane at values of less than 500 ppm by weight.

The examples below serve to further illustrate the procedure according to the invention.

EXAMPLE 1

The reactor comprised a vertical glass tube (internal diameter 2.05 cm, height 100 cm, volume 330 cm$^3$), which was surrounded by a jacket in which thermostatic water was circulated at 30 or 50° C. by pumping. The entire glass apparatus was colored brown and additionally wrapped in aluminum foil in order to exclude light-initiated photochlorination effects. All the vent openings were provided with molecular sieve drying tubes in order to prevent the incursion of atmospheric moisture. Chlorine gas was added, via a darkened glass tube filled with quartz wool and acting as a mixer, to the 1,2-dichloroethane to which had been added 2500 ppm by weight of benzene. The chlorine gas was metered via a calibrated bubble counter with hexachlorobutadiene as the barrier liquid. The metering of the liquid to the mixer was carried out via a calibrated drip device, and the metered amount was 360 cm$^3$/h. The reaction tube was packed to various levels with steel wool from STAX, fine quality, material No. 1.0313, having a bulk density of about 0.22 g/cm$^3$. The liquid reaction mixture charged with various concentrations of free chlorine was passed, after leaving the reaction space, into a receiver containing alternately an aqueous potassium iodide solution for the iodometric determination of chlorine with 0.01M sodium thiosulfate solution or 0.01M hydrochloric acid for the complexometric determination of iron(III) chloride after extraction from the organic phase. After separation of the aqueous phase, the organic phase was dried over sodium sulfate until anhydrous and subsequently analyzed by gas chromotography for benzene, monochlorobenzene, dichlorobenzene and trichlorobenzene.

The results of the individual experiments are shown in Table 1.

The numbers in the Table 1 may be interpreted as follows:

Benzene conversion during the chlorination in both cases greater than 99.8%; residence time in experiment A 55 minutes, in experiment B 33 minutes; flow rate in both cases 0.03 cm/s.

The "selectivity" of the chlorination of benzene as a function of the excess of chlorine is as follows:

|  | Benzene conversion in Mol % to | | |
| --- | --- | --- | --- |
|  | Mono- | Di- | Trichlorobenzene |
| At a Cl$_2$ excess of 180 ppm by weight | 60 | 30 | 10 |
| At a Cl$_2$ excess of 90 ppm by weight | 90 | 7 | 3 |

It can be seen from this that the specific consumption of chlorine per mol of benzene increases considerably with increasing excess of chlorine.

COMPARATIVE EXAMPLE 1

The experiments were carried out analogously to Example 1, but the steel wool was replaced by iron turnings having a bulk density of about 0.85 g/cm$^3$ or by iron(III) chloride in a concentration of 550 ppm by weight.

Even at a residence time of 200 minutes, a reaction temperature of 50° C. and a 300 ppm by weight excess of chlorine in the reaction product, measured after leaving the reaction space, analysis also showing 500 or 550 ppm by weight of iron(III) chloride in the reaction product, the benzene conversion was only 64% or 68%.

EXAMPLE 2

In the pyrolysis of 74.6 t/h of 1,2-dichloroethane to give 28.1 t/h of vinyl chloride and 16.5 t/h of hydrogen chloride (59.8% conversion), 30 t/h of unreacted 1 2-dichloroethane contaminated by 6 ppm by weight of 1,1,2-trichloroethane, 50 ppm by weight of ethyl chloride, 1500 ppm by weight of 2-chlorobuta-1,3-diene, 150 ppm by weight of 1-chlorobuta-1,3-diene and about 200 ppm by weight of predominantly unknown di-, tri-, and tetrachlorinated diolefins having 2 to 6 carbon atoms, and traces of chlorobenzenes, were produced at the bottom of the vinyl chloride column under a pressure of 6 bar absolute. After cooling to 30° C., the unreacted 1,2-dichloroethane was treated with 10 ppm by weight of o-cresol and freed from low-boiling, chlorinatable impurities by adding 0.843 kmol/h of evaporated liquid chlorine or 0.1944 kmol/h of gaseous ethylene (for removal of the excess of chlorine after the chlorination step).

The unreacted 1,2-dichloroethane from the pyrolysis of 1,2-dichloroethane and pretreated in this way now contained 476 ppm by weight of 1,1,2-trichloroethane, 50 ppm by weight of ethyl chloride and 100 ppm by weight of 2,3-dichlorobuta-1,3-diene, and was thus free from 2-chlorobuta-1,3-diene and 1-chlorobuta-1,3-diene and other chlorinated diolefins. The free chlorine content was 2 ppm by weight and iron(III) chloride was present only in traces (<2 ppm by weight). In addition, about 300 ppm by weight of benzene was also present as a consequence of prior repeated circulation.

In order to prevent further accumulation of benzene, 3 t/h of the unreacted 1,2-dichloroethane pretreated in this way was now passed at 30° C. through a cylindrical steel reactor having the following dimensions: internal diameter 1250 mm, height 2500 mm, volume 3.05 m$^3$. The steel cylinder was filled with 3 m$^3$ of steel wool from Stax, fine quality, material No. 1.0313, having a bulk density of about 0.22 g/cm$^3$. Before entering the reactor, this stream was mixed with 760 1(S.T.P.)/h of chlorine gas. At a residence time of around 75 minutes and a flow rate of about 0.055 cm/s, the 1,2-dichloroethane leaving the chlorination reactor had the following composition:

| | |
| --- | --- |
| <10 ppm by weight | of benzene |
| 391 ppm by weight | of monochlorobenzene |
| 45 ppm by weight | of dichlorobenzene |
| 7 ppm by weight | of trichlorobenzene |
| 532 ppm by weight | of iron(III) chloride |
| 80 ppm by weight | of free chlorine |
| 506 ppm by weight | of 1,1,2-trichloroethane |
| 50 ppm by weight | of ethyl chloride |
| <10 ppm by weight | of 2,3-dichlorobuta-1,3-diene |

The "ring-chlorinated" unreacted 1,2-dichloroethane was subsequently subjected to acid and alkaline washing together with a 45.5 t/h of crude 1,2-dichloroethane from the direct chlorination and oxychlorination of ethylene (weight ratio about 45:55), and fed to a low-boiling component column for dewatering with simultaneous removal of the low-boiling components. The product from the bottom of this low-boiling component column was fed to a high-boiling component column together with the remaining 27 t/h of unreacted 1,2-dichloroethane which is free from chloroprene, but still contains 300 ppm by weight of benzene. About 74 t/h of pure 1,2-dichloroethane containing around 20 ppm by weight of ethyl chloride and no iron(III) chloride were removed from the head of the high-boiling component column.

Although this purified 1,2-dichloroethane had been subjected to incomplete pyrolysis which constantly provided benzene, and the unreacted 1,2-dichloroethane was constantly circulated in accordance with the procedure described in this example, it was possible to keep the benzene level in the 1,2-dichloroethane fed to the cracking furnace at values less than 200 ppm by weight for a period of 4500 hours. The furnace run time before the next decoking was 6 months.

COMPARATIVE EXAMPLE 2

The procedure was analogous to Example 2, but without the benzene chlorination step according to the invention. A 1,2-dichloroethane whose benzene level rose to about 5000 ppm by weight in the course of 3000 hours was produced for the pyrolysis. It was only possible to achieve a furnace run time of about 4 months. In order to achieve a comparable conversion, it was necessary to successively increase the product temperature from 495 to 510° C. (temperature at the coil end).

TABLE 1

| Experiment | Amount of chlorine gas cm$^3$ (S.T.P.)/h | | Reaction temperature °C. | | Steel wool packing level cm$^3$ | |
|---|---|---|---|---|---|---|
| A | 554 | | 30 | | 100 | |
| B | 415 | | 50 | | 60 | |

| | Analysis of the course of the reaction for | | | | | |
|---|---|---|---|---|---|---|
| | | | | mono- | di- | tri- |
| | Cl$_2$ | FeCl$_3$ | benzene | | chlorobenzenes | |
| Experiment | ppm by weight | ppm by weight | ppm by weight | ppm by weight | ppm by weight | ppm by weight |
| A | 180 | 479 | <10 | 2155 | 1408 | 580 |
| B | 90 | 389 | <10 | 3230 | 326 | 177 |

We claim:

1. A process for purifying unreacted 1,2-dichloroethane, containing impurities such as benzene produced at the bottom of the vinyl chloride column in the preparation of vinyl chloride due to incomplete pyrolysis of 1,2-dichloroethane, which comprises
    a) bringing said unreacted 1,2-dichloroethane recovered from the pyrolysis of 1,2-dichloroethane into contact with liquid and/or gaseous chlorine in a chlorination reactor in the liquid phase at a residence time of 20 to 150 minutes, at temperatures of from 20 to 80° C., in the presence of an iron catalyst having a bulk density of from 0.1 to 0.5 g/cm$^3$ and filling the entire reaction space, in such amounts that the unreacted 1,2-dichloroethane leaving the reactor contains excess, free chlorine in dissolved form in concentrations of from 20 to 200 ppm by weight, based on unreacted 1,2-dichloroethane, and
    b) purifying the 1,2-dichloroethane treated with chlorine in accordance with a) by acid and alkali washing and by distillative removal of the low- and high-boiling components, including chlorinated benzenes.

2. A process for purifying unreacted 1,2-dichloroethane, produced at the bottom of the vinyl chloride column in the preparation of vinyl chloride due to incomplete pyrolysis of 1,2-dichloroethane, which comprises first treating said unreacted 1,2-dichloroethane with from 0.0001 to 0.01% by weight, based on unreacted 1,2-dichloroethane, of hydroxyl-containing aromatic compounds and subjecting it to a chlorination step and subsequent dechlorination step at temperatures between 0 and 80° C. and pressures of from 0.5 to 6 bar, and then dividing the stream of 1,2-dichloroethane into two parts and only treating a first part of the stream with chlorine as claimed in claim 1a and then purifying this first part stream by acid and alkaline washing, then freeing this first part stream, from low-boiling components and passing it to the high-boiling component column, and passing the second part stream directly to the high-boiling component column, avoiding the chlorination step, the washer and the low-boiling component removal step.

3. The process as claimed in claim 1 or 2, wherein the flow rate of the unreacted 1,2-dichloroethane is between 0.01 and 0.1 cm/s, based on the free reactor cross-section.

* * * * *